US00PP10562P

United States Patent [19]

Sys et al.

[11] Patent Number: Plant 10,562

[45] Date of Patent: Aug. 18, 1998

[54] STEVIA PLANT NAMED 'RSIT 94-1306'

[75] Inventors: Elizabeth Ann Sys; Albert Anthony Marsolais; James Brandle, all of Ontario, Canada

[73] Assignee: Royal-Sweet International Technologies Ltd. Part., Vancouver, Canada

[21] Appl. No.: 652,712

[22] Filed: May 29, 1996

[51] Int. Cl.[6] ..... A01H 5/00

[52] U.S. Cl. ..... Plt./100

[58] Field of Search ..... Plt./100

*Primary Examiner*—James R. Feyrer
*Assistant Examiner*—Kent L. Bell
*Attorney, Agent, or Firm*—Klarquist Sparkman Campbell Leigh & Whinston, LLP; Robert H. Barrigar; Alan E. Dow

[57] ABSTRACT

A new and distinctive variety of Stevia characterized by a high ratio of stevioside to rebaudioside C, a high ratio of stevioside to rebaudioside A, and a high ratio of stevioside to dulcoside A.

2 Drawing Sheets

BACKGROUND OF THE INVENTION

The present invention relates to a new and distinct variety of Stevia (*Stevia rebaudiana* Bertoni), referred to by the varietal name 'RSIT 94-1306'.

Eight steviol glycosides with sweetening properties have been identified in leaf tissues of stevia. The four major glycosides are: stevioside, rebaudioside A, rebaudioside C, and dulcoside A. The chemical structures of these compounds are shown in FIG. 1. Each of these steviol glycosides has unique sensory properties, and they can be used singly or in combination to provide a sweetener that has sensory properties tailored to a specific use. Stevia sweeteners are non-caloric, making them suitable for diabetics and weight-conscious consumers, and pH-stable and heat-stable, making them useful in a wide range of bottled beverages, confectioneries, baked goods, and dairy and canned products. For reviews of the use of stevia as a source of sweeteners, see, e.g., Handro and Ferreira, 1989, Lee 1982, and Phillips, 1987.

We set out to develop stevia varieties with high concentrations of individual steviol glycosides that could be extracted and recombined in ratios suitable for specific product uses. Landrace stevia has a combination of steviol glycosides that is not optimal for all product applications.

We discovered our new variety in a cultivated area at the Agriculture and Agri-Food Canada Research Station near Delhi, Ontario, Canada ("Delhi Research Station"). The following unique combination of characteristics is outstanding in 'RSIT 94-1306' and distinguishes it from its parents and all other stevia varieties of which we are aware: (1) a high ratio of stevioside to rebaudioside C; (2) a high ratio of stevioside to rebaudioside A; and (3) a high ratio of stevioside to dulcoside A.

This variety has not been observed under all possible environmental conditions. The following observations, measurements and comparisons describe plants grown under conditions that are similar to those generally used in commercial practice.

Asexual reproduction of this new variety by shoot-tip and stem cuttings was performed at the Delhi Research Station and showed that the foregoing characteristics are established and transmitted through succeeding asexual propagations.

BRIEF DESCRIPTION OF THE PHOTOGRAPHS

The accompanying photographs show typical specimens of this new variety, depicted in color as nearly true as is reasonably possible in a color photograph of this character. The photographs were taken at the Delhi Research Station in February 1996.

DETAILED DESCRIPTION

In 1989, seed of a landrace stevia variety from China was increased in a greenhouse at the Delhi Research Station by inter-pollination. In the summer of 1990, approximately 1000 plants were grown. Fifteen plants were selected from this population and designated SR1 through SR15. Crowns of these plants were dug out of the field in the fall of 1990 and grown in a greenhouse in the fall and winter of 1990–1991. These plants were inter-crossed and half sib seed collected from each parent plant.

In the summer of 1991, these half sib families were evaluated in a genetic heritability trial (Brandle and Rosa, 1992). One of the entries in this trial was the SR2 half sib population.

In the summer of 1994, SR2 and several other half sib populations were evaluated. 'RSIT 94-1306' was selected from the SR2 half sib population on the basis of its agronomic traits and steviol glycoside profile, based on replicated trials conducted at the Delhi Research Station.

Table 1 shows the leaf yield (kg/ha), height (cm), and lodging of 'RSIT 94-1306' as compared with 'Brazil', an open-pollinated landrace variety of stevia and the most widely grown stevia variety in Brazil.

TABLE 1

Agronomic traits of 'RSIT 94-1306' and 'Brazil'

| Variety | Leaf Yield (kg/ha) | Height (cm) | Lodging (0–9)[1] |
|---|---|---|---|
| 94-1306 | 2523 | 52 | 2.0 |
| Brazil | 2052 | 61 | 4.5 |

[1]Lodging is based on a scale of 0–9 where 0 = no lodging and 9 = all the plants lodged flat on the ground at harvest. A rating of 2 indicates that a few plants were leaning at an angle at harvest.

Table 2 shows steviol glycoside profiles in leaves of 'RSIT 94-1306,' SR2, the maternal parental population from which 'RSIT-1306' was selected, and 'Brazil'. In particular, the following were examined (on a dry weight basis): percent dulcoside A (% dulc.), percent stevioside (% stev.), percent rebaudioside C (% reb.C), percent rebaudioside A (% reb.A), and percent total glycosides (% total=% dulc.+% stev.+% reb.C+% reb.A).

TABLE 2

Steviol glycoside profiles of 'RSIT 94-1306', SR2, and 'Brazil'

| Variety | Year | % dulc. | % stev. | % reb. C | % reb. A | % Total |
|---|---|---|---|---|---|---|
| 94-1306 | 1994 | 1.12 | 17.25 | nd[1] | nd[1] | 18.37 |
| SR2 | 1994 | 1.02 | 13.07 | 0.16 | 0.41 | 14.83 |
| Brazil | 1995 | 0.25 | 7.61 | 0.54 | 3.00 | 11.40 |

[1]nd = none detected

'RSIT 94-1306' was dug out of the field in the fall of 1994 and vegetatively propagated at the Dehli Research Station by shoot-tip and stem cuttings. The stability of the steviol glycoside and agronomic traits of 'RSIT 94-1306' was verified in replicated trials conducted in 1995.

Taxonomic Description of 'RSIT 94-1306'

Figure 1:
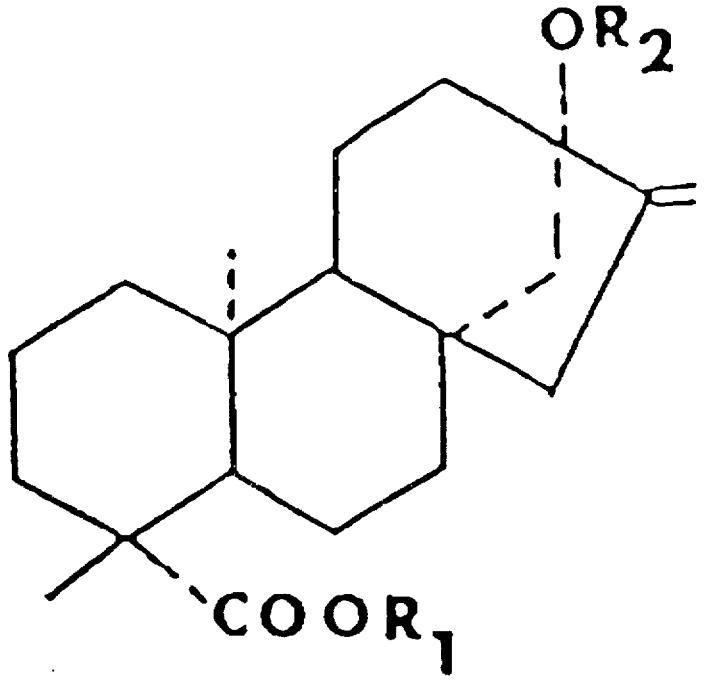
FIG. 1 shows the chemical structure of four major steviol glycoside sweeteners in stevia, stevioside, rebaudioside A, rebaudioside C, and dulcoside A.
Figure 2:
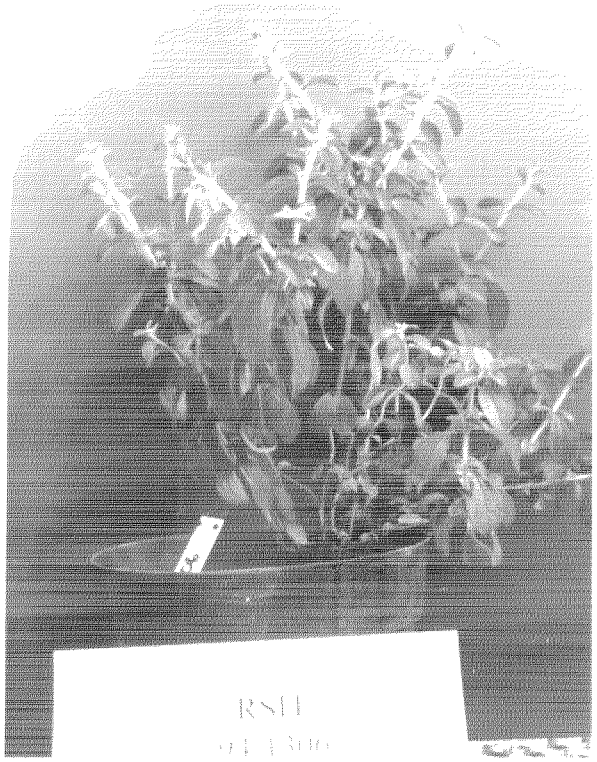
FIG. 2 is a view of a plant of the present invention.
Figure 3:
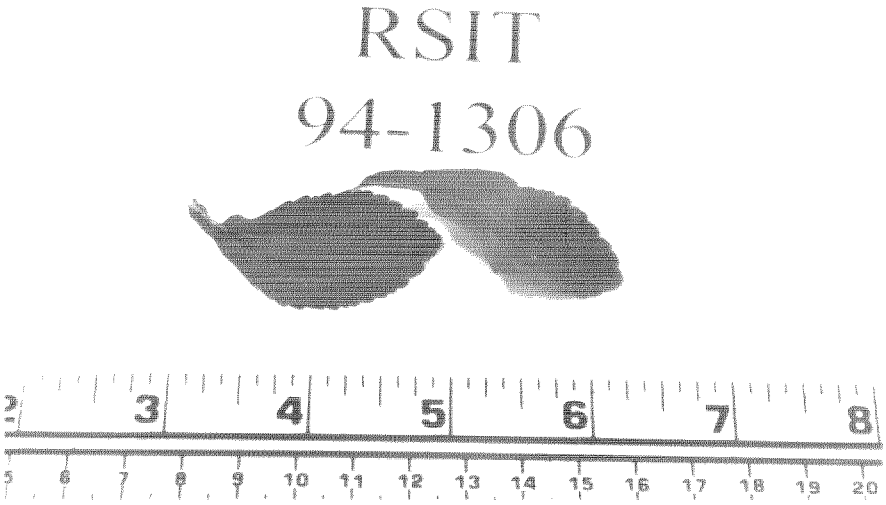
FIG. 3 is an enlarged view of leaves of the plant of FIG. 2.

'RSIT 94-1306' is a suffrutescent, erect perennial (FIG. 2). Field-grown plants may attain a height of 1.1 meters, but more commonly have a height of 6–8 dm. The stems are round, pubescent, and have internodes of medium length. The leaves are simple, opposite, sessile, exstipulate, and oblanceolate. The leaf apices are obtuse and the leaf margins are crenate above the middle and entire on a cuneately narrow base. The leaves are three-nerved and conspicuously veiny. The leaf surface is puberulent with short glandless hairs. The largest cauline leaves are up to 8 cm long and 4 cm wide and are often proliferous in the axils (FIG. 3).

The inflorescence is loosely paniculate with the heads appearing opposite the bracts in irregular sympodial cymes. The flower corollas have a pale purple throat and white limb. The seed are nearly uniform achenes, 15–17 aristate (Robinson, 1930).

Method of Determining Steviol Glycosides and Concentrations

Fresh leaf samples were harvested from field-grown stevia plants and stored in a freeze prior to extraction. Samples were freeze dried, ground to pass through a 40-mesh screen, and again freeze dried before extraction. Ground, freeze-dried plant material (300 mg) was weighed into a 15 ml polypropylene centrifuge tube (Fisher). Ten ml of 1:1 (v/v) acetonitrile-water (acetonitrile from Caledon Laboratories Ltd., Georgetown, Ontario, 190 HPLC grade) was added to each sample. Sample tubes were suspended in an ultrasonic bath at maximum ultrasonication (#9) for 15 min (Lab-line Inst. model #9333, Melrose Park, Ill.) with occasional stirring and rotation to ensure optimal extraction. Sample tubes were then centriguged at 1500 rpm for 15 min (International Centrifuge, Model V Size 2, International Equipment, Boston, Mass.). The extraction solvent was transferred to a volumetric flask with a Pasteur pipette. For routine analyses, duplicate extractions were utilized and the solvent transferred to a 25 ml volumetric flask filled to volume with acetonitrile. Samples were filtered through a 0.45 micron filter (Acrodisc 13, Gelman Sciences, Ann Arbor, Mich.).

Analyses were performed on a liquid chromatograph (Hewlett-Packard 1090) equipped with a three-channel solvent delivery system, auto sampler, and diode array detector interfaced with a chem station. Stevioside, rebaudioside A, rebaudioside C, and dulcoside A standards were obtained from FWB Chemical Consulting Ltd., Calgary, Alberta, Canada. Stevioside was also obtained from Sigma Chemical Co., St. Louis, Mo. Due to the wide variation in plant material analyzed, co-eluting peaks occasionally were apparent in the chromatogram. Often these plant constituents were eliminated filtration through a Waters NH2 Sep-Pak cartridge (Part No. WATO 20535) prior to analysis. For routine analyses, only stevioside was used as a standard. The response factor found for stevioside was used for the other three steviol glycosides after correcting for differences in molecular weight. In order to monitor this assumption during the sample determinations, a standard sample of rebaudioside A was analyzed after each calibration.

The chromatographic column was a Waters cartridge carbohydrate column (Part No. WAT 044355) having an inside diameter of 250×4.6 mm. The guard column was a carbohydrate sentry guard column (Part No. WAT 046895). The "A" solvent was $H_2O$ (pH 5.25 with AcOH), the "B" solvent was acetonitrile, and the "C" solvent was acetonitrile. The flow rate was 1.5 ml/min. The time table for use of solvents A, B, and C is found in Table 3.

TABLE 3

Time table for use of Solvent A ($H_2O$, pH 5.25 with AcOH), Solvent B (acetonitrile), and Solvent C (acetonitrile)

| Time (min.) | % Solvent A | % Solvent B | % Solvent C |
|---|---|---|---|
| 0 | 13 | 43 | 44 |
| 12 | 17.5 | 41 | 41.5 |
| 26 | 24 | 38 | 39 |
| 26.1 | 13 | 43 | 44 |

The post time was six minutes and the elution times for the steviol glycosides were 14.5 minutes for dulcoside A, 18.8 minutes for stevioside, 20.4 minutes for rebaudioside C, and 23.5 minutes for rebaudioside A. Retention times of the components of interest decreased with extensive use of the column. It was usually sufficient to simply reduce the amount of water in the initial chromatographic conditions to restore the retention times. Individual columns have been used for more than one thousand samples. Guard columns typically were replaced after about 300 samples or when system pressure became excessive. Periodically the column was washed with water to remove other plant constituents which accumulated on the column. Steviol glycosides were identified by retention time and concentrations were determined by an external standards method.

Steviol glycosides may be produced from leaves or other parts of 'RSIT 94-1306' and formulated into a sweetener for use in the food industry or by consumers by any conventional method. See, e.g., U.S. Pat. No. 4,892,938. Purified extract solutions may be directly added to a foodstuff or beverage, for example, in liquid form or converted to a crystalline form. The sweetness intensity of steviol glycosides is usually about 150 to 300 times that of sucrose, depending on the concentration of the steviol glycosides used. If desired, stevia extracts can be suitably diluted with a conventional diluent, e.g., a tasteless soluble starch, to achieve a sweetness intensity approximately that of sugar (i.e., sucrose). For convenient use by the consumer, a unit of a stevia sweetener, e.g., an amount having a total sweetness comparable to that of a standard lump of sugar, can be packaged for commercial distribution in small paper bags or in other forms known in the art. Steviol glycosides from 'RSIT 94-1306' can be used singly on in combination with steviol glycosides from other stevia varieties or with other conventional sweeteners to provide a sweetener composition that has sensory properties tailored to a specific use.

All publications and published patent documents citied in this specification are incorporated herein by reference to the same extent as if each individual publication or patent application was specifically and individually indicated to be incorporated by reference.

References Cited

Brandle, J., Rosa, N. (1992). "Heritability for Yield, Leaf:Stem Ratio and Stevioside Content Estimated from a Landrace Cultivar of *Stevia rebaudiana.*" *Can. J. Plant Sci.* 72:1263–1266.

Handro, W., Ferreira, C.M. (1989). "Stevia rebaudiana (Bert.) Bertoni: Production of Natural Sweeteners." In: *Biotechnology in Agriculture and Forestry,* vol. 7, Medicinal and Aromatic Plants II (ed. Y.P.S. Bajaj), Springer Verlag, Berlin, Heidelberg, pp. 468–487.

Lee, J. I., et al. (1982). "New High Rebaudioside-A Stevia Variety 'Suweon 11'." *Res. Rept. ORD* 24(C):186–188.

Phillips, K.C. (1987). "Stevia: Steps in Developing a New Sweetener." In: *Developments in Sweeteners*-3, Elsevier Applied Science, London (ed: T. H. Grenby), pp. 1–43.

Robinson, R. L. (1930). *Contributions from the Gray Herbarium of Harvard University XC,* The Gray Herbarium of Harvard University, Cambridge, Mass. pp. 78–91.

U.S. Pat. No. 4,892,938 (1990).

We claim:

1. A new and distinctive variety of Stevia plant, substantially as herein shown and described.

* * * * *

STRUCTURES

| | $R_1$ |
|---|---|
| Stevioside | glc $^{2}$-glc |
| Rebaudioside A | glc $^{2}$,$^{3}$ glc glc |
| Rebaudioside C | glc $^{2}$,$^{3}$ rham glc |
| Dulcoside A | glc $^{2}$-rham |

glc ; glucose
rham ; rhamnose